(12) United States Patent
Huang et al.

(10) Patent No.: US 11,675,266 B2
(45) Date of Patent: Jun. 13, 2023

(54) PHOTOSENSITIVE COMPOUND, PHOTOSENSITIVE COMPOSITION, AND PATTERNING METHOD

(71) Applicant: INDUSTRIAL TECHNOLOGY RESEARCH INSTITUTE, Hsinchu (TW)

(72) Inventors: Yao-Jheng Huang, Taipei (TW); Te-Yi Chang, Taoyuan (TW); Chin-Hua Chang, Sanwan Township (TW); Ming-Tzung Wu, Mailiao Township (TW); Yu-Ying Hsu, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 17/481,961

(22) Filed: Sep. 22, 2021

(65) Prior Publication Data

US 2022/0334480 A1 Oct. 20, 2022

Related U.S. Application Data

(60) Provisional application No. 63/175,173, filed on Apr. 15, 2021.

(51) Int. Cl.
*C07C 309/76* (2006.01)
*G03F 7/031* (2006.01)
*G03F 7/032* (2006.01)

(52) U.S. Cl.
CPC ............ *G03F 7/031* (2013.01); *C07C 309/76* (2013.01); *G03F 7/032* (2013.01); *C07C 2603/24* (2017.05)

(58) Field of Classification Search
CPC ....... G03F 7/031; G03F 7/032; C07C 309/76; C07C 2603/24
See application file for complete search history.

(56) References Cited

U.S. PATENT DOCUMENTS

| | | | |
|---|---|---|---|
| 3,046,121 A | 7/1962 | Schmidt | |
| 3,102,809 A | 9/1963 | Endermann | |
| 3,969,118 A * | 7/1976 | Stahlhofen | G03F 7/105 430/326 |
| 5,965,320 A * | 10/1999 | Torimitsu | G03F 7/2006 430/326 |
| 8,968,983 B2 | 3/2015 | Kim et al. | |
| 2005/0221222 A1 | 10/2005 | Ito et al. | |
| 2007/0275327 A1 | 11/2007 | Ito et al. | |
| 2011/0236825 A1 | 9/2011 | Park et al. | |
| 2011/0287360 A1 | 11/2011 | Lee et al. | |
| 2012/0052438 A1 | 3/2012 | Kim et al. | |

FOREIGN PATENT DOCUMENTS

| | | |
|---|---|---|
| CN | 1292890 A | 4/2001 |
| CN | 101154040 B | 6/2012 |
| CN | 103605261 A | 2/2014 |
| CN | 103309511 B | 4/2016 |
| CN | 106715477 B | 10/2018 |
| CN | 107108773 B | 5/2019 |
| DE | 872154 C | 3/1953 |
| EP | 1 724 640 A1 | 11/2006 |
| JP | 2-273749 A | 11/1990 |
| JP | 6-219348 A | 8/1994 |
| JP | 2003-201324 A | 7/2003 |
| JP | 2005-274594 A | 10/2005 |
| JP | 2007-328090 A | 12/2007 |
| JP | 2009-63824 A | 3/2009 |
| JP | 6140506 B2 | 5/2017 |
| JP | 2021-135507 A | 9/2021 |
| TW | 201413374 A | 4/2014 |
| WO | WO 2013/161942 A1 | 10/2013 |

OTHER PUBLICATIONS

Smith, Michael B.. (2013). March's Advanced Organic Chemistry—Reactions, Mechanisms, and Structure (7th Edition). John Wiley & Sons. (Year: 2013).*
Cipolloni et al., "Effects of solvent, excitation wavelength, and concentration on the photobehavior of some diazonaphthoquinones", ARKIVOC, vol. 2011, issue 9, 2011, pp. 205-220.
Taiwanese Notice Of Allowance and Search Report for Taiwanese Application No. 110140524, dated Aug. 2, 2022.
Takano et al., "Photosensitive Polyimides Developable with Basic Aqueous Solutions (II)", Journal of Applied Polymer Science, vol. 46, Issue 7, 1992, pp. 1137-1146.

(Continued)

Primary Examiner — Peter L Vajda
Assistant Examiner — Jayson D Cosgrove
(74) Attorney, Agent, or Firm — Birch, Stewart, Kolasch & Birch, LLP

(57) ABSTRACT

A patterning method includes providing a photosensitive composition on a material layer. The photosensitive composition includes one part by weight of a photo sensitive compound, 1.5 to 8 parts by weight of a resin, and 10 to 40 parts by weight of a diluent. The photosensitive compound has a chemical structure of

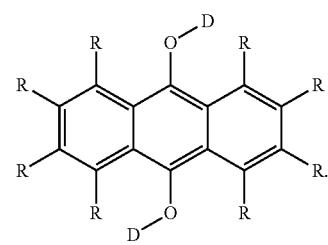

The patterning method further includes removing the diluent in the photosensitive composition to form a photoresist layer, exposing the photoresist layer, and removing an exposed part of the photoresist layer to expose a part of the material layer.

10 Claims, No Drawings

(56) References Cited

OTHER PUBLICATIONS

Abdallah et al., "Coumarin Derivatives as Photoinitiators in Photo-Oxidation and Photo-Reduction Processes and Kinetic Model for Simulations of the Associated Polymerization Profiles", ACS Appl. Polym. Mater., 2020, 2, 7, pp. S1-S26.
Abdallah et al., "In Silico Design of Nitro-Coumarins as Near-UV Photoinitiators: Towards Interesting Opportunities in Composites and 3D Printing Technologies", ACS Appl. Polym. Mater., 2020, 2, 7, pp. S1-S37.
Freddi et al., "Design of new 3-ketocoumarins for UV LED Curing", UV+EB Technology, 2016, Issue 3, total 5 pages.
Li et al., "Highly efficient dandelion-like near-infrared light photoinitiator for free radical and thiol-ene photopolymerizations", Nature Communications, 2019, 10: 3560, pp. 1-9.
Wu et al., "Coumarin Derivatives of Anion Recognition Characteristics", Imaging Science and Photochemistry, Jan. 2012, vol. 30, No. 1, pp. 43-52 (see English abstract, p. 52).
Japanese Notice of Allowance for Japanese Application No. 2021-201580 dated Nov. 22, 2022.

\* cited by examiner

PHOTOSENSITIVE COMPOUND, PHOTOSENSITIVE COMPOSITION, AND PATTERNING METHOD

CROSS REFERENCE TO RELATED APPLICATIONS

This application claims the benefit of U.S. Provisional Application No. 63/175,173 filed on Apr. 15, 2021, the entirety of which is incorporated by reference herein.

TECHNICAL FIELD

The technical field relates to a photoresist for digital lithography technology (DLT).

BACKGROUND

The photoresist is used in the lithography etching process in manufacturing scaled-down electronic components (e.g. computer chips, integrated circuits, light-emitting diode devices (LED), displays, etc.). In general, a film of a photosensitive composition is first applied onto a material layer. The diluent in the photosensitive composition is then evaporated by baking to form a photoresist layer on the material layer. The photoresist layer is then exposed to induce the chemical reaction in the exposed region of the photoresist layer. The exposed region (e.g. in the positive type photoresist) or the non-exposed region (e.g. in the negative type photoresist) of the photoresist layer is dissolved and removed by a developer after the exposure process.

The photosensitizer for the conventional positive type photoresist has a major absorption wavelength at 365 nm, which should be collocated with a photomask and cannot be used in digital lithography technology with an exposure light source of about 403 nm. Accordingly, a photosensitizer having an absorption wavelength at about 400 nm is called for to facilitate the photoresist being used in digital lithography technology.

SUMMARY

One embodiment of the disclosure provides a photosensitive compound, having a chemical structure of:

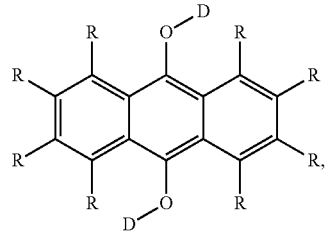

wherein each of R is independently of hydrogen, $C_{1-10}$ alkyl group, hydroxy group, or $C_{1-10}$ alkoxy group; and D is

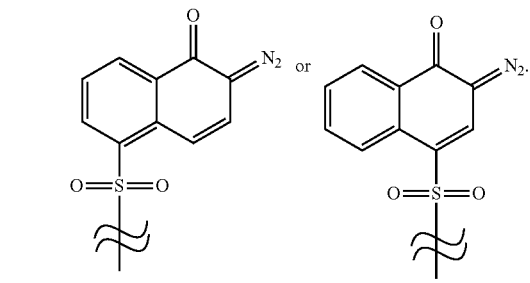

One embodiment of the disclosure provides a photosensitive composition, including: 1 part by weight of the described photosensitive compound; 1.5 to 8 parts by weight of a resin; and 10 to 40 parts by weight of a diluent.

One embodiment of the disclosure provides a patterning method, including: providing the described photosensitive composition on a material layer; removing the diluent in the photosensitive composition to form a photoresist layer; exposing the photoresist layer; and removing an exposed part of the photoresist layer to expose a part of the material layer.

A detailed description is given in the following embodiments.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details.

One embodiment of the disclosure provides a photosensitive compound, having a chemical structure of:

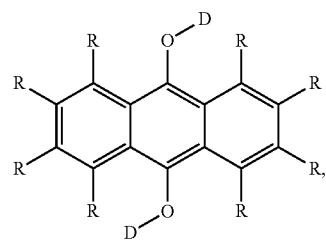

wherein each of R is independently of hydrogen, $C_{1-10}$ alkyl group, hydroxy group, or $C_{1-10}$ alkoxy group; and D is

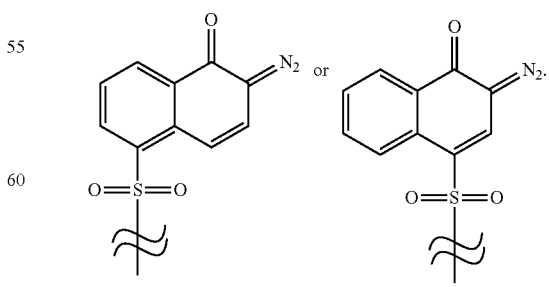

In one embodiment, the photosensitive compound is synthesized by chemically reducing the anthraquinone. Thereafter, anthraquinone in a chemically reduced state can be reacted with sulfonyl halide-containing diazonaphthoquinone (DNQ), as shown below:

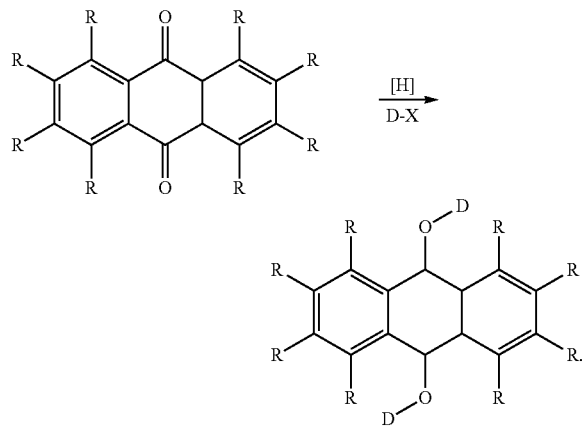

In the above formula, D-X is

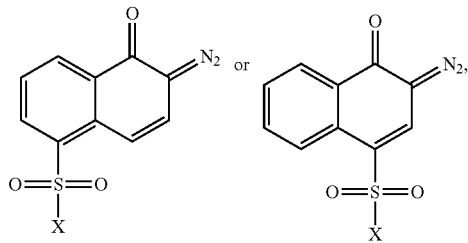

and X can be Cl, Br, or I. Note that the above reaction is one possible way, and the disclosure is not limited thereto. One skilled in the art may adopt other reactants and synthesis strategy to synthesize the photosensitive compound.

One embodiment of the disclosure provides a photosensitive composition, including: 1 part by weight of the described photosensitive compound; 1.5 to 8 parts by weight of a resin; and 10 to 40 parts by weight of a diluent. If the amount of resin is too low, the exposed part of the photoresist layer will remain as residue after development. If the amount of resin is too high, the pattern after development will peel off easily. If the amount of diluent is too low, the coating uniformity will be negatively influenced. If the amount of diluent is too high, the coating film will be overdeveloped because it is too thin.

In some embodiments, the resin includes novolac resin, epoxy resin, or another suitable resin. In some embodiments, the novolac resin includes meta-cresol (m-cresol) and para-cresol (p-cresol), and the m-cresol and the p-cresol have a weight ratio of 40:60 to 60:40. If the m-cresol amount is too low, it will easily result in a residue problem because the novolac resin will dissolve too slowly in the alkaline solution. If the m-cresol amount is too high, the pattern will peel off easily because the novolac resin will dissolve too quickly in the alkaline solution. In some embodiments, the novolac resin has a weight average molecular weight of 5000 to 15000. If the weight average molecular weight of the novolac resin is too low, it will have poor etching resistance. If the weight average molecular weight of the novolac resin is too high, it can easily result in a residue problem, because the novolac resin will dissolve too slowly in the alkaline solution.

In some embodiments, the photosensitive composition has a light absorption wavelength at 400 nm to 420 nm. In some embodiments, the photosensitive composition has a light absorption wavelength at 403 nm. This wavelength range is suitable for digital lithography technology and another maskless lithography process, but the photosensitive composition of the disclosure is not limited thereto. For example, a photoresist layer formed from the photosensitive composition of the disclosure can be exposed to a light source through a photomask.

In some embodiments, the diluent includes propylene glycol monomethyl ether acetate, cyclohexanone, N-methylpyrrolidone, methyl ethyl ketone, dimethyl sulfoxide, or a combination thereof. In addition, the photosensitive composition may include another constituent, such as leveling agent, photoacid generator, another additive, or a combination thereof, to further modify the properties of the photosensitive composition.

One embodiment of the disclosure provides a patterning method, including: providing the described photosensitive composition on a material layer; removing the diluent in the photosensitive composition to form a photoresist layer; exposing the photoresist layer; and removing an exposed part of the photoresist layer to expose a part of the material layer. The above patterning method is the general lithography steps, which is characterized by the photoresist utilizing the photosensitive composition (and the photosensitive compound) of the disclosure. In some embodiments, the step of exposing the photoresist layer includes digital lithography technology with an exposure light source having a wavelength at 400 nm to 420 nm. In some embodiments, the exposure light source has a wavelength at 407 nm. In some embodiments, the method further removing or implanting the exposed part of the material layer. For example, the material layer is a metal layer, and the step of removing the exposed part of the material may form a metal line. When the material layer is a semiconductor layer such as a silicon layer, the step of implanting the exposed part of the material may form a doped well region or source/drain regions of a transistor. Thereafter, the patterned photoresist layer can be removed by ashing or stripping.

Below, exemplary embodiments will be described in detail so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

EXAMPLES

In the following Examples, the novolac resin was commercially available from Asahi, in which the meta-cresol and the para-cresol had a weight ratio of 60:40, and the novolac resin had a weight average molecular weight of 8000 to 14000. In the photosensitive composition, the photosensitive group equivalent ratio means photosensitizer mole times diazonaphthoquinone (DNQ) substitution degree.

In the following Examples, the photosensitive composition was coated on a glass substrate to form a film, and then dried to form a photoresist layer with a thickness of 1 μm. The photoresist layer was exposed to an exposure light source of digital lithography technology, and then developed to test the development window of time. The exposure light source had a wavelength at 403 nm and an exposure intensity of 35 mJ/cm$^2$. The pattern resolution after the development was observed by an optical microscope (OM), and the adhesion force between the pattern and the glass substrate was measured according to the standard ASTM D3359 to determine the applicable range of the photoresist layer.

Synthesis Example 1

5.0 g of anthraquinone, 8.36 g of sodium hyposulfite, 50 mL of tetrahydrofuran (THF), and 50 mL of de-ionized water were mixed to perform a chemical reduction reaction at room temperature, to form anthraquinone in a chemically reduced state. 12.90 g of 2-diazo-1,2-naphthoquinone-5-sulfonyl chloride was dissolved in 50 g of THF to form a sulfonyl chloride-containing DNQ solution. The solution of the anthraquinone in a chemically reduced state was added to the sulfonyl chloride-containing DNQ solution, then heated to 40° C. and mechanically stirred at 300 rpm to react for 10 minutes, and then heated to 50° C. and mechanically stirred at 300 rpm to react for 60 minutes. The reaction result was cooled and then poured into de-ionized water, and then the organic layer was collected to be concentrated. The concentrate was filtered, and the filtered cake was washed with methanol/water solution. The filtered cake was dried to obtain the product. The product had the $^1$H NMR spectrum (d$_6$-DMSO) as below: δ6.34(c), δ7.42(b), δ7.75~7.77(f) and (g), δ7.96(d), δ8.03(e), δ8.40(a). The chemical structure of the product was shown below:

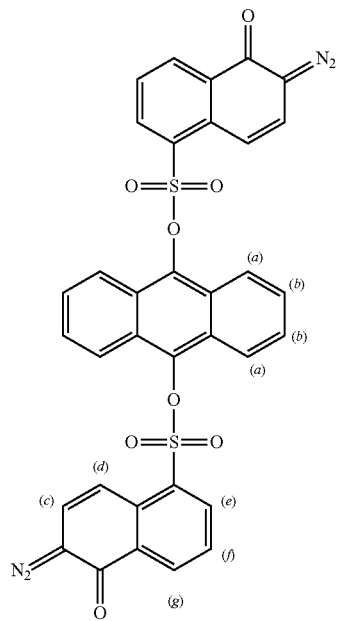

Synthesis Example 2

Synthesis Example 2 was similar to Synthesis Example 1, and the difference in Synthesis Example 2 was the substitution position of the sulfonyl chloride group in the sulfonyl chloride-containing DNQ being different. The other reactant amounts and the reaction conditions of Synthesis Example 2 were similar to those of Synthesis Example 1. The product had the $^1$H NMR spectrum (d$_6$-DMSO) as below: δ7.32(f), δ 7.36(g), δ7.38(c), δ7.42(d), δ7.53(d), δ7.65(e), δ8.40(a). The chemical structure of the product was shown below:

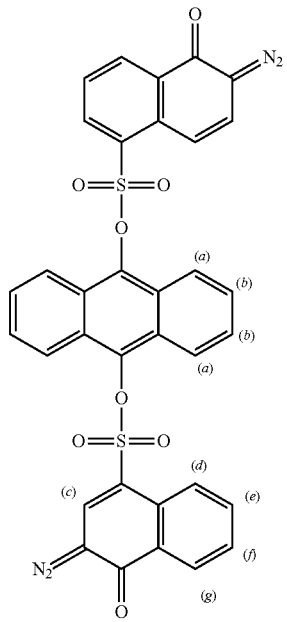

Synthesis Example 3

12.92 g of 2-diazo-1,2-naphthoquinone-5-sulfonyl chloride was dissolved in 50 g of THF to form a sulfonyl chloride-containing DNQ solution. 3.85 g of dihydroxy anthraquinone was dissolved in 100 mL of THF, and then added to the sulfonyl chloride-containing DNQ solution, then heated to 40° C. and mechanically stirred at 300 rpm to react for 10 minutes, and then heated to 50° C. and mechanically stirred at 300 rpm to react for 60 minutes. The reaction result was cooled and then poured into de-ionized water, and then the organic layer was collected to be concentrated. The concentrate was filtered, and the filtered cake was washed with methanol/water solution. The filtered cake was dried to obtain the product. The product had the $^1$H NMR spectrum (d$_6$-DMSO) as below: δ5.3(d), δ6.85(a), δ6.9(e), δ7.55(c), δ7.61~7.7(g) and (h), δ7.80(b), δ8.16(f). The chemical structure of the product was shown below:

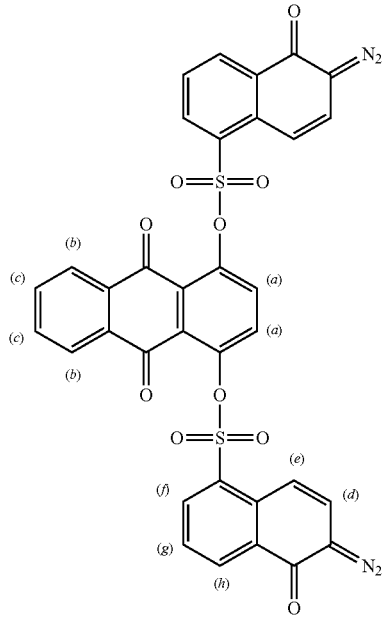

Comparative Example 1-1

2.72 g of commercially available photosensitizer A (2,3,4-trihydroxybenzophenone naphthoquinone-1,2-diazido-5-sulfonate commercially available from Miwon), 13.78 g of the novolac resin, and 83.50 g of propylene glycol monomethyl ether acetate (PGMEA) were mixed to form a photosensitive composition, in which the photosensitive group equivalent ratio was 0.84. The development window of the photoresist layer from the photosensitive composition was >180 seconds, but the pattern peeled off without an adhesion force. The chemical structure of the commercially available photosensitizer A is shown below:

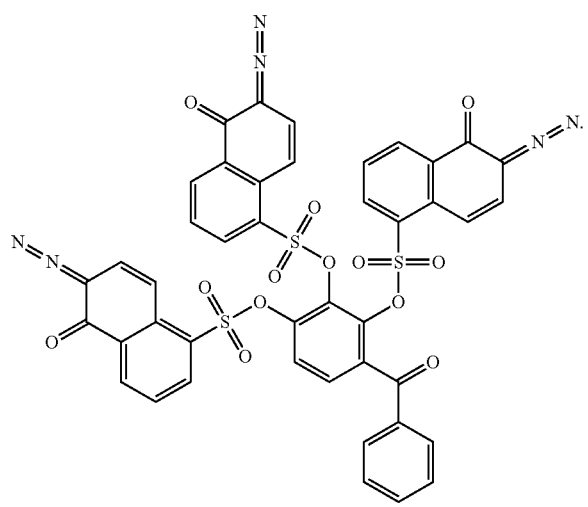

Comparative Example 1-2

4.24 g of commercially available photosensitizer A, 12.26 g of the novolac resin, and 83.50 g of PGMEA were mixed to form a photosensitive composition, in which the photosensitive group equivalent ratio was 1.18. The development window of the photoresist layer from the photosensitive composition was >180 seconds, the pattern resolution was 50 μm, and the adhesion force between the pattern and the glass substrate was 5B.

Comparative Example 2-1

2.71 g of the product in Synthesis Example 3, 13.79 g of the novolac resin, and 83.50 g of PGMEA were mixed to form a photosensitive composition, in which the photosensitive group equivalent ratio was 0.84. The development window of the photoresist layer from the photosensitive composition was >180 seconds, but the pattern peeled off without an adhesion force.

Comparative Example 2-2

4.23 g of the product in Synthesis Example 3, 12.27 g of the novolac resin, and 83.50 g of PGMEA were mixed to form a photosensitive composition, in which the photosensitive group equivalent ratio was 1.18. The development window of the photoresist layer from the photosensitive composition was >180 seconds, the pattern resolution was 50 μm, and the adhesion force between the pattern and the glass substrate was 5B.

Example 1-1

1.67 g of the product in Synthesis Example 1, 14.83 g of the novolac resin, and 83.50 g of PGMEA were mixed to form a photosensitive composition, in which the photosensitive group equivalent ratio was 0.56. The development window of the photoresist layer from the photosensitive composition was >240 seconds, but the pattern peeled off without an adhesion force.

Example 1-2

2.71 g of the product in Synthesis Example 1, 13.79 g of the novolac resin, and 83.50 g of PGMEA were mixed to form a photosensitive composition, in which the photosensitive group equivalent ratio was 0.84. The development window of the photoresist layer from the photosensitive composition was 60 seconds to 180 seconds, the pattern resolution was 30 μm, and the adhesion force between the pattern and the glass substrate was 5B.

Example 1-3

3.41 g of the product in Synthesis Example 1, 13.09 g of the novolac resin, and 83.50 g of PGMEA were mixed to form a photosensitive composition, in which the photosensitive group equivalent ratio was 1. The development window of the photoresist layer from the photosensitive composition was 60 seconds to 180 seconds, the pattern resolution was 10 μm, and the adhesion force between the pattern and the glass substrate was 5B.

Example 1-4

4.23 g of the product in Synthesis Example 1, 12.27 g of the novolac resin, and 83.50 g of PGMEA were mixed to form a photosensitive composition, in which the photosensitive group equivalent ratio was 1.18. The development window of the photoresist layer from the photosensitive composition was 60 seconds to 180 seconds, the pattern resolution was 20 μm, and the adhesion force between the pattern and the glass substrate was 5B.

Example 1-5

5.18 g of the product in Synthesis Example 1, 11.32 g of the novolac resin, and 83.50 g of PGMEA were mixed to form a photosensitive composition, in which the photosensitive group equivalent ratio was 1.36. The development window of the photoresist layer from the photosensitive composition was >240 seconds, and the exposed part that should be removed was partially remained as residue.

Example 2-1

1.67 g of the product in Synthesis Example 2, 14.83 g of the novolac resin, and 83.50 g of PGMEA were mixed to form a photosensitive composition, in which the photosensitive group equivalent ratio was 0.56. The development window of the photoresist layer from the photosensitive composition was >240 seconds, but the pattern peeled off without an adhesion force.

Example 2-2

2.71 g of the product in Synthesis Example 2, 13.79 g of the novolac resin, and 83.50 g of PGMEA were mixed to form a photosensitive composition, in which the photosensitive group equivalent ratio was 0.84. The development window of the photoresist layer from the photosensitive composition was 60 seconds to 180 seconds, the pattern resolution was 30 μm, and the adhesion force between the pattern and the glass substrate was 5B.

Example 2-3

3.41 g of the product in Synthesis Example 2, 13.09 g of the novolac resin, and 83.50 g of PGMEA were mixed to form a photosensitive composition, in which the photosensitive group equivalent ratio was 1. The development window of the photoresist layer from the photosensitive composition was 60 seconds to 180 seconds, the pattern resolution was 10 μm, and the adhesion force between the pattern and the glass substrate was 5B.

Example 2-4

4.23 g of the product in Synthesis Example 2, 12.27 g of the novolac resin, and 83.50 g of PGMEA were mixed to form a photosensitive composition, in which the photosensitive group equivalent ratio was 1.18. The development window of the photoresist layer from the photosensitive composition was 60 seconds to 180 seconds, the pattern resolution was 20 and the adhesion force between the pattern and the glass substrate was 5B.

Example 2-5

5.18 g of the product in Synthesis Example 2, 11.32 g of the novolac resin, and 83.50 g of PGMEA were mixed to form a photosensitive composition, in which the photosensitive group equivalent ratio was 1.36. The development window of the photoresist layer from the photosensitive composition was >240 seconds, and the exposed part that should be removed was partially remained as residue.

The properties of the photoresist layer in Examples and Comparative Examples are tabulated in Table 1:

TABLE 1

| | Photosensitive group equivalent ratio | Development window | Resolution (μm) | Adhesion force |
|---|---|---|---|---|
| Comparative Example 1-1 | 0.84 | >180 s | Peeling | — |
| Comparative Example 1-2 | 1.18 | >180 s | 50 μm | 5B |
| Comparative Example 2-1 | 0.84 | >180 s | Peeling | — |
| Comparative Example 2-2 | 1.18 | >180 s | 50 μm | 5B |
| Example 1-1 | 0.56 | >240 s | Peeling | — |
| Example 1-2 | 0.84 | 60-180 s | 30 μm | 5B |
| Example 1-3 | 1 | 60-180 s | 10 μm | 5B |
| Example 1-4 | 1.18 | 60-180 s | 20 μm | 5B |
| Example 1-5 | 1.36 | >240 s | Residue | — |
| Example 2-1 | 0.56 | >240 s | Peeling | — |
| Example 2-2 | 0.84 | 60-180 s | 30 μm | 5B |
| Example 2-3 | 1 | 60-180 s | 10 μm | 5B |
| Example 2-4 | 1.18 | 60-180 s | 20 μm | 5B |
| Example 2-5 | 1.36 | >240 s | Residue | — |

Compared to the commercially available photosensitizer, the photosensitizer in the disclosure resulted in a wider adjustable range of the photosensitive group equivalent ratio, the wider development window of time, the higher pattern resolution. The photoresist formula including the photosensitizer of the disclosure had a high flexible adjustment and a high resolution.

It will be apparent to those skilled in the art that various modifications and variations can be made to the disclosed methods and materials. It is intended that the specification and examples be considered as exemplary only, with the true scope of the disclosure being indicated by the following claims and their equivalents.

What is claimed is:
1. A photosensitive compound, having a chemical structure of:

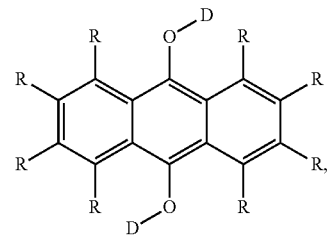

wherein each of R is independently of hydrogen, $C_{1-10}$ alkyl group, hydroxy group, or $C_{1-10}$ alkoxy group; and D is

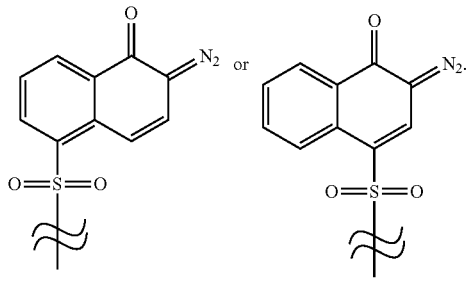

2. A photosensitive composition, comprising:
   1 part by weight of the photosensitive compound as claimed in claim 1;
   1.5 to 8 parts by weight of a resin; and
   10 to 40 parts by weight of a diluent.
3. The photosensitive composition as claimed in claim 2, wherein the resin comprises novolac resin or epoxy resin.
4. The photosensitive composition as claimed in claim 3, wherein the novolac resin comprises meta-cresol and para-cresol, and the meta-cresol and the para-cresol have a weight ratio of 40:60 to 60:40.
5. The photosensitive composition as claimed in claim 3, wherein the novolac resin has a weight average molecular weight of 5000 to 15000.
6. The photosensitive composition as claimed in claim 2, having a light absorption wavelength at 400 nm to 420 nm.
7. The photosensitive composition as claimed in claim 2, wherein the diluent comprises propylene glycol monomethyl ether acetate, cyclohexanone, N-methylpyrrolidone, methyl ethyl ketone, dimethyl sulfoxide, or a combination thereof.
8. A patterning method, comprising:
   providing the photosensitive composition as claimed in claim 2 on a material layer;

removing the diluent in the photosensitive composition to form a photoresist layer;
exposing the photoresist layer; and
removing an exposed part of the photoresist layer to expose a part of the material layer.

9. The patterning method as claimed in claim 8, wherein the step of exposing the photoresist layer comprises digital lithography technology with an exposure light source having a wavelength at 400 nm to 420 nm.

10. The patterning method as claimed in claim 8, further removing or implanting the exposed part of the material layer.

* * * * *